(12) United States Patent
Capuder

(10) Patent No.: US 6,369,219 B2
(45) Date of Patent: *Apr. 9, 2002

(54) PREPARATION OF CLAVULANATE SALTS

(75) Inventor: Egidij Capuder, Krtina (SI)

(73) Assignee: LEK Pharmaceutical & Chemical Co. DD, Ljubjana (SI)

( * ) Notice: Subject to any disclaimer, the term of this patent is extended or adjusted under 35 U.S.C. 154(b) by 0 days.

This patent is subject to a terminal disclaimer.

(21) Appl. No.: 09/738,434

(22) Filed: Dec. 14, 2000

Related U.S. Application Data

(63) Continuation of application No. 08/930,527, filed as application No. PCT/GB96/00921 on Apr. 17, 1996, now Pat. No. 6,180,782.

(30) Foreign Application Priority Data

Apr. 20, 1995 (SL) .............................................. 9500134

(51) Int. Cl.$^7$ ........................................... C07D 503/08
(52) U.S. Cl. ..................................................... 540/349
(58) Field of Search ......................................... 540/349

(56) References Cited

U.S. PATENT DOCUMENTS

| | | | |
|---|---|---|---|
| 4,110,165 A | 8/1978 | Cole et al. | |
| 4,144,242 A | 3/1979 | Fleming et al. | |
| 4,454,069 A | 6/1984 | Cook et al. | |
| 4,647,659 A | 3/1987 | Cook et al. | |
| 4,650,795 A | 3/1987 | Liberman et al. | |
| 6,180,782 B1 * | 1/2001 | Capuder ..................... | 540/349 |

FOREIGN PATENT DOCUMENTS

| | | |
|---|---|---|
| EP | 0 312 813 A3 | 4/1989 |
| EP | 0 562 583 A1 | 9/1993 |
| EP | 0 594 099 A1 | 4/1994 |
| WO | WO 93/25557 | 12/1993 |
| WO | WO94/21647 | 9/1994 |
| WO | WO94/22873 | 10/1994 |
| WO | WO 95/21173 | 8/1995 |
| WO | WO 95/23870 | 9/1995 |
| WO | WO96/20199 | 7/1996 |
| WO | WO96/26944 | 9/1996 |

OTHER PUBLICATIONS

Harris, et al., "The Cross–flow Filtration of an Unstable β–lactam Antibiotic Fermentation Broth", J. Chem. Tech. Biotechnol, 1998, vol. 42, pp. 19–30.

"Einsatz der Membranfiltration zur Herstellung von Antibiotika", Chemi–Technik, 15. Jahrgang, 1986, Mr. 6, pp. 73–75.

Grant IR, et al., "The Recovery of the Secondary Metabolite Clavulanic Acid from Streptomyces Clavuligerus Fermentation Broth by Ultrafiltration", University College London, The 1993 Icheme Research Event, pp. 173–175.

Moo–Young, Murray, "The Principles, Applications and Regulations of Biotechnology in Industry, Agriculture and Medicine", Comprehensive Biotechnology, University of Waterloo, The Principles of Biotechnology:Engineering Considerations, vol. 2, 1985, pp. 349–366.

* cited by examiner

*Primary Examiner*—Mark L. Berch
(74) *Attorney, Agent, or Firm*—Beyer Weaver & Thomas, LLP

(57) ABSTRACT

Provided is a process for purification of clavulanic acid or a pharmaceutically acceptable salt or ester thereof, including adding an additional solvent to a solution of clavulanic acid in water immiscible solvent; contacting the solution with an amine; isolating the amine salt of the clavulanic acid formed; and converting the amine into clavulanic acid or a pharmaceutically acceptable salt or ester thereof.

12 Claims, No Drawings

PREPARATION OF CLAVULANATE SALTS

This application is a continuation of prior application Ser. No. 08/930,527, now U.S. Pat. No. 6,180,782, which is a 371 of PCT/GB96/00921 filed Apr. 17, 1996.

This invention relates to a process for preparation of pharmaceutically acceptable salts of clavulanic acid, particularly but not exclusively alkali salts especially potassium clavulanate.

Clavulanic acid is the common name for (2R,5R,Z)-30 (2-hydroxyethylidene)-7-oxo-4-oxa-1-azabicyclo[3.2.0] heptane-2-carboxylic acid. Clavulanic acid and its alkali metal salts and esters are active as inhibitors of beta lactamase produced by some Gram positive as well as Gram negative micro-organisms. In addition to inhibition of beta lactamase, clavulanic acid and alkali metal salts thereof also have a synergistic action with penicillin and cephalosporin antibiotics. Clavulanic acid and its salts are used in pharmaceutical preparations to prevent the deactivation of beta lactam antibiotics. Commercial preparations contain potassium clavulanate in combination with amoxycillin trihydrate. Potassium clavulanate is more stable than the free acid or other salts.

Clavulanic acid is prepared by fermentation of a microorganism such as strains of Streptomyces such as *S.clavuligerus* NRRL 3585, *S.jimonjinensis* NRRL 5741 and *S.katsurahamanus* IFO 13716 and Streptomyces sp.P6621 FERM P2804. The aqueous culture obtained after fermentation is purified and concentrated in accordance with conventional processes for example filtration and chromatographic purification as disclosed in GB 1508977, prior to extraction of the aqueous solution with an organic solvent to obtain a solution of impure clavulanic acid in the solvent.

GB 1508977 discloses preparation of clavulanate salts by filtration of the fermentation broth by passage through an anionic exchange resin. This process may achieve acceptable yields but sophisticated chromatographic purification methods are required and the use of resin columns involves substantial investment for manufacture on a commercial scale.

GB 1543563 discloses a fermentation process wherein the pH value of the medium is maintained in the range 6.3 to 6.7. Pharmaceutically acceptable salts such as potassium clavulanate are prepared by re-salting from lithium clavulanate.

EP-A-0026044 discloses use of the tertiary butylamine salt of clavulanic acid as an intermediate for purification of clavulanic acid. This salt was known from BE862211 or DE 2733230 which disclosed that the salt was even more stable than the sodium or potassium clavulanate salts. Tertiary butylamine is a toxic compound and is also difficult to remove from waste water giving rise to serious pollution concerns.

EP-A-0562583 discloses use of salts of clavulanic acid with N,N'-monosubstituted symmetric ethylene diamines such as N,N'-diisopropyethylene diammonium diclavulanate as useful intermediates for isolation and preparation of pure clavulanic acid or alkaline metal clavulanate salts from ethyl acetate extract.

WO93/25557 discloses use of clavulanate salts with numerous amines as intermediates for preparation of clavulanic acid or pharmaceutically acceptable salts or esters.

EP-A-0594099 discloses use of tertiary octylamine with clavulanic acid as an intermediate in preparation of clavulanic acid or pharmaceutically acceptable salts.

WO94/21647 discloses use of N,N'-substituted diamines such as N,N'-diisopropylethylene diammonium diclavulanate as a useful intermediate for preparation of clavulanic acid and alkali salts.

WO94/22873 discloses use of novel tertiary diammonium salts of clavulanic acid such as N,N,N',N'-tetramethyl-1,2-diaminoethane clavulanate as a useful intermediate for preparation of clavulanic acid and salts thereof.

The aim of this invention is to prepare clavulanic acid and its pharmaceutically acceptable salts, such as potassium clavulanate in a new and simple manner, wherein the desired substance is obtained in a high yield and of high purity.

According to the present invention a process for preparation and/or purification of clavulanic acid or a pharmaceutically acceptable salt or ester thereof, including the steps of:

a. adding an additional solvent to a solution of clavulanic acid in a water immiscible solvent;

b. contacting the solution with an amine;

c. isolating the amine salt of clavulanic acid formed; and d. converting the amine salt into clavulanic acid or a pharmaceutically acceptable salt or ester thereof.

The clavulanic acid may be obtained by fermentation of a Streptomyces micro-organism such as Streptomyces sp.P6621 FERM P2804 as disclosed in JP Kokai 80-162993. Alternative Clavulanic acid producing Streptomyces strains such as *S.Clavuligerus* may be employed.

Solids may be removed from the fermentation broth by filtration or preferably by microfiltration.

Microfiltration of the broth may be carried out as disclosed in WO95/23870. In a preferred process according to this disclosure the aqueous fermentation broth containing crude clavulanic acid, mycelium, proteins and other suspended solid matter is purified by microfiltration at a pH value between 5.8 and 6.2 and a temperature about 20 to 40° C. The purified filtrate may be concentrated by reverse osmosis and then directly extracted in a series of countercurrent centrifugal extractors with a water immiscible solvent, preferably ethyl acetate. The extraction is preferably carried out at a temperature between 15 to 25° C. and a pH between 1 and 3. The extract is then dried to a water content below 0.1 mol. %, further concentrated by evaporation and decolorised with active charcoal to obtain a completely dry organic phase.

The concentration of crude clavulanic acid in the dry concentrated extract in the water immiscible solvent such as ethyl acetate may be between 8 g/l and 40 g/l, preferably between 20 g/l and 40 g/l.

Alternative water immiscible solvents include: methyl acetate, propyl acetate, n-butly acetate, methyl ethyl ketone, methyl isobutyl ketone and mixtures thereof.

The additional solvent may be selected from: alcohols, nitriles, ketones and mixtures thereof. Preferred additional solvent include $C_1$ to $C_6$ alcohols, acetonitrile acetone and mixtures thereof.

Especially preferred solvents are selected from: methanol, ethanol, isopropanol, n-butanol, isobutanol and acetonitrile. Methanol is the most preferred solvent.

The amine may be selected from tertiary butylamine, benzyl tertiary butylamine, tertiary octylamine adamantane amine and sec butylamine. Other amines which have been proposed for purification of clavulanic acid may be employed.

In a preferred embodiment of the invention the amine is of formula I

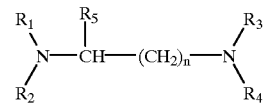

wherein the substituents $R^1$, $R^2$, $R^{3,}$ and $R^4$ are independently: hydrogen; $C_1$ to $C_8$ straight or branched alkyl; $C^2$ to $C^4$ hydroxyalkyl or wherein the groups $NR^1R^2$ and $NR^3R^4$ jointly denote a heterocyclic ring having 3 to 6 methylene groups bound to a nitrogen atom, one of these groups being optionally substituted with an oxygen or a sulphur atom or by an imino group; wherein $R^5$ denotes hydrogen or methyl; and n is an integer from 1 to 3.

Especially preferred amines are symmetrical N,N'-alkylene diamines, preferably N,N'-diisopropylethylene diamine, N,N'-diethylethylene diamine, N,N'-dibenzylethylene diamine, N,N,N',N'-tetramethylethylene diamine. N,N'-diisopropylethylene diamine is especially preferred.

At least one equivalent of the selected alkylene diamine, preferably a 10% excess up to about 2 molar equivalents may be employed for preparation of the clavulanate ammonium salt.

In a preferred embodiment of the invention the reaction of clavulanic acid with N,N'-monosubstituted symmetric diamines can be carried out in a mixture of ethyl acetate and methanol for example having 0 to 80% of methanol, preferably in the ratio 4:1 to 2:1, preferably 3:1.

Use of a mixture of ethyl acetate and methanol according to the present invention allows isolation of the diammonium diclavulanate salt free of undesired impurities such as clavam-2-carboxylate. The clavam-2-carboxylic acid is difficult to separate from clavulanic acid (see D Brown et al, JCS, Chem.Com. 1979, 282). According to the United States Pharmacopoeia US P23, page 385, 1995 no more than 0.01% of potassium clavam-2-carboxylate is permitted.

Surprisingly it has been discovered that the yield of the intermediary salts with N,N'-monosubstituted symmetric diamines is substantially higher and is almost quantitative when the transformation is carried out in a mixture of solvents, preferably ethyl acetate and methanol, in comparison to the transformation carried out in a single solvent, for example as disclosed in U.S. Pat. No. 5,310,898.

The ammonium diclavulanate salts prepared in accordance with this invention may be used as intermediate compounds for preparation of completely pure clavulanic acid and its pharmaceutically acceptable salts such as potassium clavulanate. Akali metal clavulanate salts may be prepared using an appropriate source of alkali metal, for example potassium 2-ethyl hexanoate in isopropanol (the solvent containing between 0% and 4% water). Alternative alkali metal salts include alkali carbonates, bicarbonates, or hydroxides, organic carboxylic acids, alkanoic acid salts such as acetates, propionates, hexanoates of which potassium 2-ethyl hexanoate is especially preferred. Suitable salts in accordance with the present invention are pharmaceutically acceptable alkali salts such as the sodium, potassium, calcium and magnesium salts of which sodium and potassium, especially potassium are preferred. The invention is further described by means of example but in any limitative sense.

REFERENCE EXAMPLE

N,N'-diisopropylethylenediammonium diclavulanate

A dried concentrated extract of crude clavulanic acid in ethyl acetate was prepared in accordance with known methods, for example as disclosed in WO95/23870. The clavulanic acid content was 32 g/l and the water content was below 2 g/l. The ethyl acetate extract (500 cm³) was decolorised by treatment with 5 g/l of activated charcoal. N,N'-diisopropylethylenediamine (10 cm³) was added during 10 min with vigorous stirring. The solution was stirred for a further 15 min and the precipitate was separated. The precipitate was washed with 2×50 cm³ portions of acetone and dried under vacuum (1 hr, 100 mbar, 40° C.). N,N'-diisopropylethylenediammonium diclavulanate (24 g, yield 80%) was obtained.

Analysis:

| | |
|---|---|
| Assay of clavulanic acid: | 53.0% |
| Transparency of 2% aq. solution of N,N'-diisopropylethylenediammonium diclavulanate: | 4.4% |
| Assay of impurities: | 4.0 Area % |

Example 1

N,N'-diisopropylethylenediasmonium diclavulanate

A dried concentrated extract of crude clavulanic acid in ethyl acetate was prepared in accordance with known methods, for example as disclosed in WO95/23870. The clavulanic acid content was 32 g/l and the water content below 2 g/l.

The ethyl acetate extract (500 cm³) was decolorised by treatment with 5 g/l of activated charcoal. Methanol (165 cm³) was added followed by N,N'-diisopropylethylenediamine (10 cm³) during 10 min with vigorous stirring. The solution was stirred for a further 15 min and the precipitate was separated. The precipitate was washed with 2×50 cm³ portions of acetone, dried under vacuum (1 hr, 100 mbar, 40° C.) and N,N'-diisopropylethylenediammonium diclavulanate (25 g, yield 96%) was obtained.

Analysis:

| | |
|---|---|
| Assay of clavulanic Acid: | 61.1% |
| Transparency of 2% aq. solution of N,N'-diisopropylethylenediammonium diclavulanate: | 81.7% |
| Assay of impurities: | 0.3 Area % |

Example 2

Preparation of pure potassium clavulanate 2 (a)

N,N'-diisopropylenediammonium diclavulanate (19.4 g, 0.028 mole) prepared in accordance with Example 1 was dissolved in isopropanol (165 cm³) and water (7 cm³). The solution was further diluted with isopropanol (320 cm³) and was decolorised with active charcoal (2.5 g). The solution was filtered and potassium 2-ethyl hexanoate (2 M solution, 25 cm³) was added at room temperature during 15 min. The solution was stirred for an additional 5 min and chilled to 10° C. The product was filtered, washed with 2×5 cm³ portions of acetone and dried under vacuum at 40° C. Pure potassium clavulanate (10 g, yield 70%) was obtained as crystalline needles.

Analysis:

| | |
|---|---|
| Assay of clavulanic acid: | 83.3% |
| Transparency of 2% aq. solution of N,N'-diisopropylethylenediammonium diclavulanate: | 91.6% |
| Assay of impurities: | 0.0 Area % |

2 (b)

N,N'Diisopropylethylenediammonium diclavulanate (10.0 g, assay 62%) was added to a mixture of isopropanol (85 cm³) and water (3.5 cm³). The suspension was warmed to 27° C. to obtain a homogeneous solution. Active charcoal (3.85 g) was added. The solution was stirred for 20 min and the charcoal was removed by filtration and washed with isopropanol (45 cm³). The filtrate and isopropanol washings were combined and potassium 2-ethyl hexanoate (2 M solution in isopropanol) was added dropwise during 15 min. The mixture was cooled to 0 to 10° C. to stirred for 1 hr. The resultant crystals were filtered, washed once with isopropanol (20 cm$^3$) and washed twice with acetone (20 cm$^3$). The product was dried under vacuum at 30 to 40° C. to give potassium clavulanate (5.8 g, yield 76%, assay of clavulanic acid 81.6%).

2 (c)

N,N,N',N'-Tetramethylethylenediammonium diclavulanate (8.0 g, assay 71%) was dissolved in water (8 cm$^3$) and diluted with isopropanol (100 cm$^3$). The resultant mixture was treated with active charcoal (1.2 g), filtered and a solution of potassium 2-ethyl hexanoate (2 M in isopropanol, 19.0 cm$^3$) was added in small portions. The mixture was stirred for 30 min at room temperature and the precipitate was filtered, dried under vacuum in silica gel at room temperature to give pale yellow crystals of potassium clavulanate (5.26 g, yield 75%, assay 80.9%).

Example 3

A dried concentrated extract of clavulanic acid (20.0 g/l) in ethyl acetate was diluted with methanol (330 cm$^3$). N,N'-diisopropylethylenediamine (DIPEDA) (10.1 cm$^3$, 10% excess) was added dropwise with stirring during 10 min. The mixture was cooled to −10° C., further stirred for 30 min and the precipitate filtered, washed with acetone (2×50 cm$^3$) and dried at 30 to 40° C. at reduced pressure. Clavulanic acid DIPEDA salt (24.8 g, yield 80%, assay 64.3) was obtained.

Example 4

The procedure of Example 3 was repeated with the same amount of other alcohols and the results are shown in Table 1.

TABLE 1

Preparation of N,N'-Diisopropylethylenediamine (DIPEDA) Salt

| AMINE | ADDED SOLVENT | YIELD % | TRANS-MITTANCE (2% sol., 420 nm) | ASSAY OF CLAV. ACID (in %) | CAL-CULATED ASSAY OF THE SALT (%) |
|---|---|---|---|---|---|
| DIPEDA | / | 62 | 30 | 55.4 | 75.5 |
| DIPEDA | n-butanol | 50 | 93 | 60.9 | 83.0 |
| DIPEDA | isobutanol | 73 | 94 | 61.0 | 83.2 |
| DIPEDA | isopropanol | 84 | 90 | 66.0 | 90 |
| DIPEDA | ethanol | 69 | 89 | 53.5 | 73.0 |
| DIPEDA | methanol | 80 | 96 | 64.3 | 87.7 |

Example 5

A dried concentrated solution of clavulanic acid in ethyl acetate (300 cm$^3$, 25.2 g/l) was diluted with methanol (50 cm$^3$) and acetone (50 cm$^3$) . N,N'-diisopropylethylenediamine (4.1 cm$^3$, 20% excess) was added in small portions during 5 min. The resulted heterogeneous mixture was stirred at 0° C. for 1 hr and the precipitated product was filtered and treated as described in Example 3 to give clavulanic acid DIPEDA salt (9.61 g, yield 74%, assay 58%).

The results of analogous procedures in which the ethyl acetate extract was diluted with a mixture of different water miscible solvents is shown in Table 2.

TABLE 2

Preparation of N,N'-Diisopropylethylenediamine (DIPEDA) Salt in Three-solvent Mixtures

| AMINE | ADDED SOLVENT I | ADDED SOLVENT II | YIELD (%) | TRANS-MITTANCE (2% sol., 420 nm) | ASSAY OF CLAV. ACID (%) |
|---|---|---|---|---|---|
| DIPEDA | methanol | / | 78 | 99 | 65 |
| DIPEDA | methanol | acetone | 78 | 78 | 61 |
| DIPEDA | methanol | ethanol | 70 | 93 | 59 |
| DIPEDA | methanol | isopropanol | 75 | 94 | 61 |

Example 6

A solution of clavulanic acid in ethyl acetate (1 l, 29.8 g/l) was diluted with acetonitrile (330 cm$^3$ and the procedure was continued as described in Example 3 to give clavulanic acid DIPEDA salt crystals (38.9 g, yield 77%, assay 59%).

Example 7

A solution of clavulanic acid in ethyl acetate (1 l, 22.1 g/l) was diluted with different amounts of methanol, treated with 10% excess of N,N'-diisopropylethylenediamine and the procedure of Example 3 was followed. The results are shown in Table 3.

TABLE 3

Preparation of N,N'-Diisopropylethylenediamine (DIPEDA) Salt using different volumes of methanol

| AMINE | ADDED SOLVENT I | RATIO EtOAc/methanol | YIELD (%) | TRANS-MITTANCE (2% sol., 420 nm) | ASSAY OF CLAV. ACID (%) |
|---|---|---|---|---|---|
| DIPEDA | methanol | 0% MeOH | 77 | 88 | 57 |
| DIPEDA | methanol | 3:1 | 81 | 96 | 61 |
| DIPEDA | methanol | 2:1 | 79 | 96 | 62 |
| DIPEDA | methanol | 1:1 | 73 | 97 | 63 |

Example 8

An ethyl acetate solution of clavulanic acid (1 l, 25.2 g/l) was diluted with ethanol (33 cm$^3$) N,N'-diethylethylenediamine (10.0 cm$^3$, 10% excess) was added dropwise during 15 min with stirring and the mixture was stirred for a further 30 min. After cooling below 0° C. the mixture was filtered to give precipitated product which was washed with acetone and dried at 25° C. under reduced pressure to give 27.1 g (yield 61%, assay 71%).

Example 9

An ethyl acetate solution of clavulanic acid (1 l, 24.0 g/l) was diluted with isopropanol (330 cm$^3$). N,N,N',N'-tetramethylethylenediamine (11.0 cm$^3$, 10% excess) was added dropwise during a period of 15 min and the solution stirred for 1 hr. After cooling below 0° C., the mixture was filtered to give a precipitated product which was washed with acetone and dried under reduced pressure at 25° C. to give 12.5 g (yield 37%, assay 71%).

The result of experiments in which isopropanol was omitted or replaced with another alcohol are shown in table 5.

TABLE 5

Preparation of N,N,N',N'-Tetramethylethylenediamine (TMEDA) Salt

| AMINE | ADDED SOLVENT | YIELD (%) | TRANS-MITTANCE (2% sol., 420 nm) | ASSAY OF CLAV. ACID (%) | CAL-CULATED ASSAY OF THE SALT (%) |
|---|---|---|---|---|---|
| TMEDA | / | 30 | 81 | 72.5 | 94 |
| TMEDA | isopropanol | 37 | 97 | 71 | 92 |
| TMEDA | ethanol | 0 | | | |
| TMEDA | methanol | 0 | | | |

Example 10

An ethyl acetate solution of clavulanic acid (1 l, 24.0 g/l) was diluted with ethanol (330 cm$^3$). N,N-dibenzylethylenediamine (15.7 cm$^3$, 10% excess) was added dropwise during 15 min and the mixture was stirred for 1 hr. After cooling below 0° C. the mixture was filtered to give a precipitate which was washed with acetone and dried at 25° C. under reduced pressure to give 22.5 g (yield 54%, assay 57.3%). The results of experiments in which ethanol was omitted or replaced with other alcohols are shown in Table 6.

TABLE 6

Preparation of N,N'-Dibenzylethylenediamine (DBEDA) Salt

| AMINE | ADDED SOLVENT | YIELD (%) | TRANS-MITTANCE (2% sol., 420 nm) | ASSAY OF CLAV. ACID (%) | CAL-CULATED ASSAY OF THE SALT (%) |
|---|---|---|---|---|---|
| DBEDA | / | 3 | 73 | | |
| DEEDA | isopropanol | 31 | 93 | 58.8 | 94.4 |
| DBEDA | ethanol | 54 | 93 | 57.3 | 92.0 |
| DBEDA | methanol | 0 | | | |

Example 11

A solution of clavulanic acid in ethyl acetate (1 l, 17.5 g/l) was diluted with isopropanol (330 cm$^3$). Tert-butylamine (10.1 cm$^3$, 10% excess) was added dropwise during 15 min and the mixture stirred for 1 hr. After cooling below 0° C. the mixture was filtered to give a precipitated product which was washed with acetone and dried at 25° C. under reduced pressure to give 21.1 g (yield 77%, assay 63.8%).

Results of experiments in which isopropanol was omitted or replaced with another alcohol are shown in Table 7.

TABLE 7

Preparation of tert-Butylamine (TBA) Salt

| AMINE | ADDED SOLVENT | YIELD (%) | TRANS-MITTANCE (2% sol., 420 nm) | ASSAY OF CLAV. ACID (%) | CAL-CULATED ASSAY OF THE SALT (%) |
|---|---|---|---|---|---|
| TBA | / | 81 | 76 | 67.0 | 91.7 |
| TBA | isopropanol | 77 | 94 | 63.8 | 87.3 |
| TBA | ethanol | 43 | 96 | 65.5 | 89.6 |
| TBA | methanol | 0 | | | |

Example 12

A solution of clavulanic acid in ethyl acetate (1 l, 20.9 g/l) was diluted with ethanol (330 cm$^3$). Benzyl-tert-butylamine (21.9 cm$^3$, 10% excess) was added dropwise during 15 min and the mixture was stirred for 1 hr. After cooling below 0° C. the mixture was filtered to give a precipitated product which was washed with acetone and dried at 25° C. in vaccuo to give 27.1 g (yield 68%, assay 52.5%).

The results of experiments in which ethanol was omitted or replaced with another alcohol are shown in Table 8.

TABLE 8

Preparation of Benzyl-tert-butylamine (BTBA) Salt

| AMINE | ADDED SOLVENT | YIELD (%) | TRANSMIT-TANCE (2% sol., 420 nm) | ASSAY OF CLAV. ACID (%) | CALCULATED ASSAY OF THE SALT (%) |
|---|---|---|---|---|---|
| BTBA | / | 83 | 93 | 53.2 | 97.0 |
| BTBA | isopropanol | 67 | 90 | 52.1 | 95.0 |
| BTBA | ethanol | 68 | 94 | 52.5 | 95.7 |
| BTBA | methanol | 0 | | | |

Example 13

A solution of clavulanic acid in ethyl acetate (1 l, 18.4 g/l) was diluted with isopropanol 330 cm$^3$. Tert-octylamine (16.4 cm$^3$, 10% excess) was added dropwise during 15 min and the mixture was stirred for 1 hr. After cooling below 0° C. the mixture was filtered to give a precipitated product which was washed with acetone and dried at 25° C. under reduced pressure to give 21.6 g (yield 67%, assay 57.2%).

The results of experiments in which isopropanol was omitted or replaced with another alcohol are shown in Table 9.

TABLE 9

Preparation of tert-Octylamine (TOA) Salt

| AMINE | ADDED SOLVENT | YIELD (%) | TRANSMIT-TANCE (2% sol., 420 nm) | ASSAY OF CLAV. ACID (%) | CALCULATED ASSAY OF THE SALT (%) |
|---|---|---|---|---|---|
| TOA | / | 80 | 75 | 55.8 | 92.1 |
| TOA | isopropanol | 67 | 90 | 57.2 | 94.5 |
| TOA | ethanol | 35 | 92 | 56.8 | 93.8 |
| TOA | methanol | 0 | | | |

Example 14

A solution of clavulanic acid in ethyl acetate (1 l, 28.3 g/l) was diluted with methanol (330 cm³). 1-adamantanamine (23.7 mg, 10% excess) was added in small portions during 15 min and the mixture was stirred for 1 hr. After cooling below 0° C. the mixture was filtered to give a precipitate which was washed with acetone and dried at 25° C. under reduced pressure to give 39.6 g (yield 76%, assay 54.3%).

The results of experiments in which methanol was omitted or replaced by other alcohols are shown in Table 10.

TABLE 10

Preparation of 1-Adamantanamine (AA) Salt

| AMINE | ADDED SOLVENT | YIELD (%) | TRANSMIT-TANCE (2% sol., 420 nm) | ASSAY OF CLAV. ACID (%) | CALCULATED ASSAY OF THE SALT (%) |
|---|---|---|---|---|---|
| AA | / | 81 | 92 | 55.0 | 93.3 |
| AA | isopropanol | 76 | 89 | 53.0 | 89.9 |
| AA | ethanol | 80 | 89 | 54.0 | 91.6 |
| AA | methanol | 76 | 94 | 54.3 | 92.1 |

Example 15

A solution of clavulanic acid in ethyl acetate (1 l, 28.3 g/l) was diluted with ethanol (33 cm³). Sec-butylamine (15.8 cm³, 10% excess) was added dropwise during 15 min and the mixture was stirred for 1 hr. After cooling below 0° C. the mixture was filtered to give a precipitate which was washed with acetone and dried at 25° C. under reduced pressure to give 21.0 g (yield 52.6%, assay 70.8%).

The results of experiments in which ethanol was omitted or replaced with alcohols are shown in Table 11.

TABLE 11

Preparation of sec-Butylamine (SBA) Salt

| AMINE | ADDED SOLVENT | YIELD (%) | TRANSMIT-TANCE (2% sol., 420 nm) | ASSAY OF CLAV. ACID (%) | CALCULATED ASSAY OF THE SALT (%) |
|---|---|---|---|---|---|
| SBA | / | 8 | 65 | | |
| SBA | isopropanol | 52 | 94 | 70.3 | 96.2 |
| SBA | ethanol | 53 | 96 | 70.8 | 96.9 |
| SBA | methanol | 0 | | | |

What is claimed is:

1. A process for the preparation of a purified alkaline metal salt of clavulanic acid comprising:
   (a) removing solids from a clavulanic acid-containing fermentation broth by microfiltration to form a filtrate;
   (b) concentrating the filtrate by removal of water to form a concentrate;
   (c) extracting the concentrate with a water immiscible solvent to form an organic phase solution comprising clavulanic acid;
   (d) drying the organic phase solution;
   (e) adding an additional dry solvent selected from C1 to C6 alcohols and mixtures thereof to the dry organic phase solution;
   (f) contacting the solution with a diamine of Formula I:

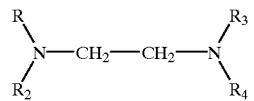

wherein the substitutents R, $R_2$, $R_3$ and $R_4$ are independently: hydrogen, $C_1$ to $C_8$ straight or branched alkyl;

(g) isolating alkylene diammonium diclavulanate formed; and (h) reacting the alkylene diammonium diclavulanate with a source of a pharmaceutically acceptable alkaline metal to form a purified alkaline metal clavulanate salt.

2. A process as claimed in claim 1, wherein the additional dry solvent is ethanol.

3. A process as claimed in claim 1, wherein the additional dry solvent is iso-propanol.

4. A process as claimed in claim 1, wherein the diamine is a symmetrical N,N'-alkylethylene diamine.

5. A process claimed in claim 1, wherein the diamine is selected from N,N'-diisopropylethylene diamine, N,N,N'N' tetramethylethylene diamine.

6. A process as claimed in claim 5, wherein the diamine is N,N'-diisopropylethylene diamine.

7. A process as claimed in claim 1 wherein the water immiscible extraction solvent is ethyl acetate.

8. A process as claimed in claim 7 wherein the ratio of ethyl acetate to alcohol is 4:1 to 2:1.

9. A process as claimed in claim 8 wherein the ratio is 3:1.

10. A process as claimed in claim 1, wherein the pharmaceutically acceptable alkaline metal is potassium.

11. A process as claimed in claim 10, wherein the source of the pharmaceutically acceptable alkaline metal is potassium-2-ethylhexanoate.

12. A process as claimed in claim 1, wherein the purified alkaline metal clavulanate salt is potassium clavulanate.

* * * * *